US00PP33031P2

(12) United States Plant Patent
Griffin

(10) Patent No.: US PP33,031 P2
(45) Date of Patent: May 4, 2021

(54) ***ALOE* PLANT NAMED 'FIRECRACKER'**

(50) Latin Name: ***Aloe* hybrid**
Varietal Denomination: FIRECRACKER

(71) Applicant: Altman Specialty Plants, Inc, Vista, CA (US)

(72) Inventor: Kelly Griffin, Carlsbad, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 16/873,345

(22) Filed: Mar. 24, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Aloe* plant named 'FIRECRACKER' is disclosed, characterized by an irregularly serrated leaf edge, intense orange-red protuberances on leaves, and a red flowered inflorescence. The new variety is an *Aloe*, typically produced as a garden or container plant.

2 Drawing Sheets

Figure 1:
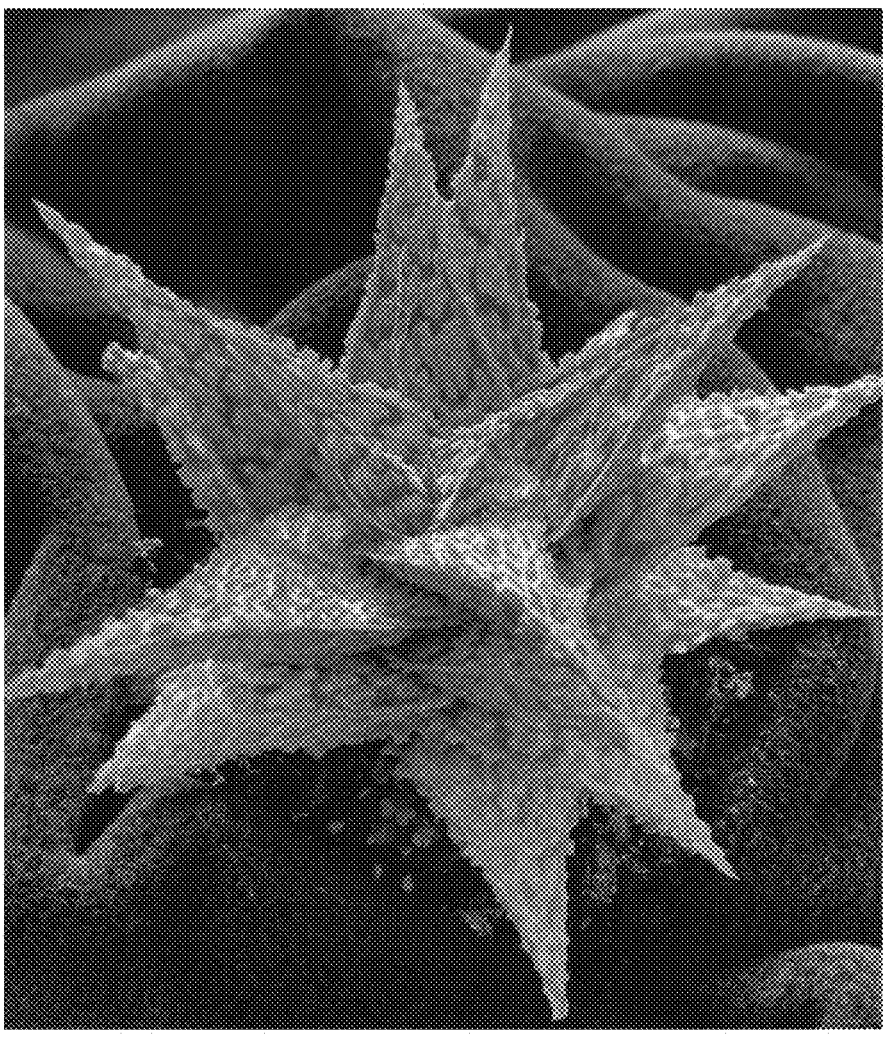

Latin name of the genus and species: *Aloe* hybrid.
Variety denomination: 'FIRECRACKER'.

BACKGROUND OF THE INVENTION

The new cultivar is a product of a planned breeding program. The seed parent is the unpatented *Aloe* hybrid 'Pink Blush'. The pollen parent is the unpatented, unnamed proprietary seedling which is a cross of *Aloe divaricata* x *Aloe intermedia* x *Aloe* cv 'Pink Blush'. The crossing was made in December 2016 at a commercial greenhouse in Vista, Calif. 'FIRECRACKER' was found and selected by the inventor in June 2017 at the same greenhouse in Vista, Calif.

Asexual reproduction of the new cultivar 'FIRECRACKER' was first performed by tissue culture at a commercial laboratory in Vista, Calif. in July 2017. 'FIRECRACKER' has since produced several generations and has shown that the unique features of this cultivar are stable and reproduced true to type.

SUMMARY OF THE INVENTION

The cultivar 'FIRECRACKER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIRECRACKER'. These characteristics in combination distinguish 'FIRECRACKER' as a new and distinct *Aloe* cultivar:

1. Serrated leaf edge.
2. Intense red protuberances on leaves.
3. Red flowered inflorescence.
4. Table top size *Aloe*, maturing at 6 to 8" across.

PARENTAL COMPARISON

Plants of the new cultivar 'FIRECRACKER' are similar to the seed parent in most horticultural characteristics. However, plants of the new variety differ from the seed parent in the following:

1. The new variety produces a more compact rosette than the seed parent.
2. The new variety has brighter, more colorful leaves than the seed parent.
3. The new variety has a redder more pronounced leaf edge than the seed parent.

Plants of the new cultivar 'FIRECRACKER' are similar to the pollen parent in most horticultural characteristics. However, plants of the new variety differ in the following:

1. The new variety is a smaller plant than the pollen parent.
2. The new variety has a different leaf shape than the pollen parent.
3. The new variety has a different leaf protuberance pattern than the pollen parent.

COMMERCIAL COMPARISON

'FIRECRACKER' can be compared to the unpatented commercial variety *Aloe* 'Delta Dawn'. The two *Aloe* varieties are similar in most horticultural characteristics; however, the new variety differs in the following:

1. Plants of the new variety are smaller and more compact than plants of this comparator.
2. The new variety has brighter and more colorful leaves than this comparator.
3. The new variety has a cleaner growth habit with better symmetry than does this comparator.

BRIEF DESCRIPTION OF THE PHOTOGRAPH PHOTOGRAPHS

The accompanying photographs illustrate in full color a typical plant of 'FIRECRACKER' grown in a greenhouse in Vista, Calif. This plant is approximately 24 months old, shown in a 15 cm container.

Figure 2:
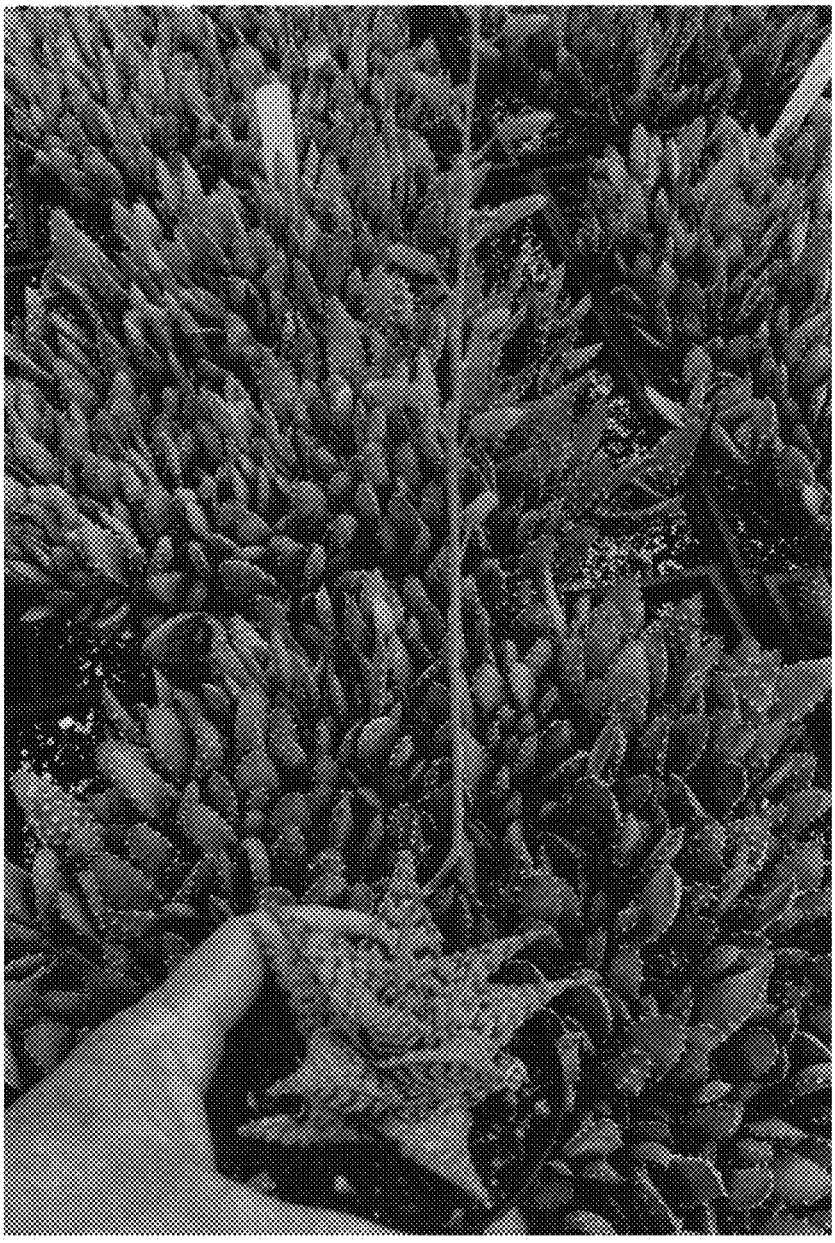

FIG. 2 illustrates the inflorescence of the new variety 'FIRECRACKER', the plants in the background are unnamed green seedlings.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'FIRECRACKER' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'FIRECRACKER'.

Age of the plant described: 2 years.

PROPAGATION

Time to initiate roots: Approximately 25 days at 22° C.

Root description: Fibrous. Brown, not accurately measured with The R.H.S. Chart.

Propagation method: Tissue culture.

PLANT

Growth habit: Upright rosette, offsetting to form clumps with time.

Container size: 9 cm.

Height: Approximately 15 cm to top of highest leaf. Approximately 50 cm to top of highest inflorescence.

Plant spread: Approximately 16 cm.

Growth rate: Moderate.

Branching characteristics: No branches, rosettes offsetting from base.

FOLIAGE

Leaf:

*Arrangement*.—Rosette.

*Average length*.—Average 12-14 cm.

*Average width*.—Average 6-8 cm.

*Shape of blade*.—Deltoid.

*Apex*.—Acuminate.

*Base*.—Clasping.

*Margin*.—Irregular serrate.

*Texture of top surface*.—Scabrous. Protuberances about 2 mm high, 21-2 mm wide and 3 to 5 mm long.

*Texture of bottom surface*.—Scabrous. Protuberances about 2 mm high, 21-2 mm wide and 3 to 5 mm long.

*Quantity of leaves per plant*.—Average 12-14.

*Color*.—Young foliage upper side: RHS Green 138C, with densely occurring, protuberances near Orange-Red N34B surrounded by blotches of Green-White 157C. Margin near Orange-Red N34B. Young foliage under side: RHS Green 138C. Mature foliage upper side: RHS Green 138C, with densely occurring, protuberances near Orange-Red 35A surrounded by blotches of White 155C. Margin near Orange-Red N34B. Mature foliage under side: RHS Green 138C.

*Venation*.—Linear. Color: Indistinguishable from leaf blade.

FLOWER

Natural flowering season: Rebloomer, three to four times a year in Southern California.

Inflorescence type and habit: Panicle, seldom branched.

Rate of flower opening: Moderate.

Flower longevity on plant: 1.5 months.

Quantity of flowers: 10 to 20.

Total inflorescence size:

*Height*.—Approximately 32 cm.

*Width*.—Approximately 8 cm.

Corolla:

*Arrangement*.—Perianth cylindrical/corolla small and reflexed.

*Length*.—Approximately 2.5 cm.

*Width*.—Approximately 1 cm at widest point.

*Tepals*.—Typically fused, the most mature flowers split at apex into 6 tepals/lobes. Unfused portion about 5 mm long and 3 mm wide.

*Color*.—Tepals: When opening: Outer surface: Near Red 42A, apex near Yellow-Green 151C. Inner surface: Near Yellow 10D, apex near Yellow-Green 151D. Fully opened: Outer surface: Near Red 42B, apex near Yellow-Green 151D. Inner surface: Near Yellow 10D, apex near Yellow-Green 150D.

Bud:

*Shape*.—Cylindrical.

*Length*.—Approximately 2.5 cm.

*Diameter*.—Approximately 0.5 cm.

*Color*.—Near Red 42A.

Peduncle:

*Length*.—Approximately 19 cm.

*Width*.—About 7 mm.

*Color*.—Near Greyed-Red 182D.

Pedicels:

*Length*.—Approximately 1 cm.

*Width*.—2 mm.

*Aspect*.—Lateral.

*Color*.—Near Red 42C, base Green 138A.

Fragrance: None.

REPRODUCTIVE ORGANS

Stamens:

*Number*.—6.

*Filament length*.—Approximately 2.5 cm.

*Filament color*.—Near White 155C.

*Anther length*.—0.25 cm.

*Anther color*.—Near Yellow 7A.

*Anther shape*.—Oval.

*Pollen color*.—Near Yellow 13B.

Pistil:

*Number*.—1.

*Length*.—Approximately 3 cm.

*Style color*.—Near White 155C.

*Stigma*.—Shape: Rounded. Color: Near White 155A. Ovary color: Near Green 138D.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C.

Disease/pest resistance: Shows mite resistance and black spot resistance (pathogen unconfirmed).

What is claimed is:

1. A new and distinct cultivar of *Aloe* plant named 'FIRECRACKER' as herein illustrated and described.

* * * * *